United States Patent
Bito et al.

(10) Patent No.: US 12,044,763 B2
(45) Date of Patent: Jul. 23, 2024

(54) MAGNETIC RESONANCE IMAGING APPARATUS, IMAGE ANALYZER, AND FLUID ANALYSIS METHOD

(71) Applicant: FUJIFILM Healthcare Corporation, Kashiwa (JP)

(72) Inventors: Yoshitaka Bito, Chiba (JP); Hisaaki Ochi, Chiba (JP)

(73) Assignee: FUJIFILM Healthcare Corporation, Chiba (JP)

(*) Notice: Subject to any disclaimer, the term of this patent is extended or adjusted under 35 U.S.C. 154(b) by 104 days.

(21) Appl. No.: 18/073,178

(22) Filed: Dec. 1, 2022

(65) Prior Publication Data
US 2023/0221391 A1    Jul. 13, 2023

(30) Foreign Application Priority Data
Jan. 13, 2022    (JP) .................. 2022-003914

(51) Int. Cl.
*G01R 33/563*    (2006.01)
*A61B 5/055*    (2006.01)

(52) U.S. Cl.
CPC ........ *G01R 33/56341* (2013.01); *A61B 5/055* (2013.01)

(58) Field of Classification Search
CPC ................ G01R 33/56341; A61B 5/055
See application file for complete search history.

(56) References Cited

U.S. PATENT DOCUMENTS

| 10,185,017 B2* | 1/2019 | Yokosawa | G01R 33/5608 |
| 10,588,523 B2* | 3/2020 | Priatna | G01R 33/5676 |
| 2010/0271021 A1* | 10/2010 | Liu | G01R 33/56341 |
| | | | 324/309 |

FOREIGN PATENT DOCUMENTS

JP    6467341    1/2019

OTHER PUBLICATIONS

European search report dated May 24, 2023 in connection with European Patent Application No. 22 211 518.
Yoshitaka Bito et al., "Low b-value diffusion tensor imaging for measuring pseudorandom flow of cerebrospinal fluid", Magnetic Resonance in Medicine 2021; 86, pp. 1369 to 1382.

* cited by examiner

*Primary Examiner* — Gregory H Curran
(74) *Attorney, Agent, or Firm* — Paul Teng

(57) ABSTRACT

Fluid parameters such as WSS and EL are accurately calculated, using flow velocity information obtained by diffusion tensor imaging. Dispersion of a flow velocity distribution of fluid is calculated, using a diffusion tensor image obtained with respect to an examination target containing fluid, and an estimation model is set for a distribution shape of intra-voxel flow velocity. Using the estimation model and the dispersion of the flow velocity distribution, a differential value of the flow velocity is calculated. Then, a fluid parameter representing a flow characteristic of the fluid is calculated.

16 Claims, 12 Drawing Sheets

EXAMPLE OF INTRA-VOXEL FLOW VELOCITY DISTRIBUTION

RECTANGULAR DISTRIBUTION (a)

NORMAL DISTRIBUTION (b)

FIG. 12A

SETTING OF IMAGING CONDITIONS 1200

- PULSE SEQUENCE: [EPI SEQUENCE]
- IMAGING PARAMETER: [FOV, TR, ITE, NUMBER OF SHOTS]
- CALCULATION OF PARAMETERS: ○ REQUIRED ● NOT REQUIRED
- FLOW VELOCITY: [LARGE]
- SITE: [ ]

FIG. 12B

SETTING OF IMAGING CONDITIONS 1200

- PULSE SEQUENCE: [EPI SEQUENCE]
- IMAGING PARAMETER: [FOV, TR, ITE, NUMBER OF SHOTS]
- CALCULATION OF PARAMETERS: ○ ● ○
- PC METHOD
- DT
- COMBINATION
- WEIGHT: [ ]

MAGNETIC RESONANCE IMAGING APPARATUS, IMAGE ANALYZER, AND FLUID ANALYSIS METHOD

BACKGROUND OF THE INVENTION

Technical Field

The present invention relates to a magnetic resonance imaging (hereinafter, abbreviated as MRI) apparatus and an analysis technique of measurement data obtained by the MRI apparatus, and in particular, to an analysis technique of a diffusion tensor image.

Description of the Related Art

Analyzing a flow of fluid that circulates human brain and body allows obtainment of effective indicators for diagnosis of various diseases. For example, fluid parameters such as wall shear stress (WSS), fluid kinetic energy (KE), and kinetic energy loss (EL), are effective indicators for detecting an abnormal flow of blood or cerebrospinal fluid, and there are proposed various techniques for measuring and analyzing those indicators.

As one of the techniques, the specification of Japanese Patent No. 6,467,341 (hereinafter, referred to as Patent Document 1) discloses a method that uses the phase contrast (PC) method of MRI to analyze kinetic energy loss and others, from obtained measurement data. In the PC method, a gradient pulse for dephasing NMR signals is combined with a gradient pulse for rephasing, thereby differentiating the phase between a signal from a stationary portion and a signal from a portion with a flow, and a velocity of fluid such as blood flow in a desired region is calculated. In the technique described in Patent Document 1, difference information of adjacent vectors is calculated from a map of velocity vector values of the fluid obtained by the PC method (a blood flow vector image having the velocity vector value as a pixel value), and then using this difference information, EL and others are calculated.

In addition, imaging methods of MRI that allows fluid observation include diffusion weighted imaging (DWI) and diffusion tensor imaging (DTI). It is reported in Magnetic Resonance in Medicine 2021; 86, pp. 1369 to 1382 (hereinafter, referred to as Non-Patent Document) that DTI is a method to show information representing anisotropy of diffusion for each voxel by a diffusion tensor, from measurement data obtained by performing DWI using MPG pulses in at least six directions, and this method is effective for observation of a flow such as pseudo-random flow of cerebrospinal fluid.

SUMMARY OF THE INVENTION

Technical Problem

In the PC method, it is required to execute repeatedly a pulse sequence for applying a rephasing gradient pulse to a dephasing gradient pulse that diffuses the phase, after a predetermined time interval, so as to acquire a signal. Thus, spatial resolution of an image is relatively low. Taking the difference between neighboring vectors in a blood flow vector image having the low spatial resolution may result in that a differential value of the flow velocity is calculated lower than an actual differential value. Therefore, there is a possibility that errors in blood flow parameter values such as EL become larger, because these fluid parameter values are obtained based on thus calculated differential value of the flow velocity. In particular, when the fluid velocity is low, such errors are likely to expand.

An object of the present invention is to provide a technique to accurately calculate the fluid parameters, using MRI. The present invention also aims at improving accuracy in the fluid parameter calculation, especially for the fluid at low velocity.

Solution to Problem

To achieve the objects as described above, the present invention uses flow velocity information obtained by diffusion tensor imaging and a model of a flow velocity distribution, to calculate a differential vector of the flow velocity, and then, the fluid parameters are obtained.

That is, an MRI apparatus of the present invention comprises a measurement unit configured to execute a pulse sequence of diffusion-weighted imaging including an MPG pulse to acquire measurement data, and a calculation unit configured to calculate a pseudo diffusion tensor having information on a flow velocity and diffusion of fluid within an examination target, using the measurement data acquired by the measurement unit, wherein the calculation unit includes a fluid parameter calculator configured to calculate a fluid parameter other than the pseudo diffusion tensor, using the pseudo diffusion tensor and an estimation model of an intra-voxel distribution of the flow velocity.

An image analyzer of the present invention is an independent analyzer having a function of the calculation unit of the MRI apparatus as described above, comprising a receiving unit configured to receive the measurement data measured in an MRI apparatus or a value of the pseudo diffusion tensor calculated from the measurement data, a calculation unit configured to calculate a fluid parameter using the measurement data or the value of the pseudo diffusion tensor received by the receiving unit, wherein the calculation unit includes a fluid parameter calculator configured to calculate the fluid parameter serving as an indicator that represents a characteristic of a flow of fluid, using the pseudo diffusion tensor, and an estimation model of a flow velocity distribution.

Further, the present invention provides a fluid analysis method using a diffusion tensor image of an examination target containing fluid, obtained by an MRI apparatus, comprising the following steps, calculating dispersion of a flow velocity of the fluid using the diffusion tensor image; calculating a differential vector of the flow velocity using the dispersion and a distribution shape of intra-voxel flow velocity; and calculating a fluid parameter representing a characteristic of a flow of the fluid, using the differential vector.

The present invention provides a novel method of calculating the fluid parameters from DTI (diffusion tensor imaging), using an estimated distribution of the fluid in a voxel. The present invention utilizes the flow velocity distribution in the voxel and avoids calculation errors associated with low resolution, unlike the PC method using the averaged flow velocity in the voxel and a difference in the flow velocity between the voxels. Accordingly, it is possible to accurately calculate the fluid parameter. Particularly for the fluid at low velocity, lowering of calculation accuracy due to reduction in spatial resolution can be prevented.

BRIEF DESCRIPTION OF THE DRAWINGS

FIGS. 12A and 12B each illustrates an example of GUI according to the third embodiment.

DETAILED DESCRIPTION OF THE PREFERRED EMBODIMENTS

There will now be described embodiments of an MRI apparatus of the present invention with reference to the accompanying drawings.

Figure 1:
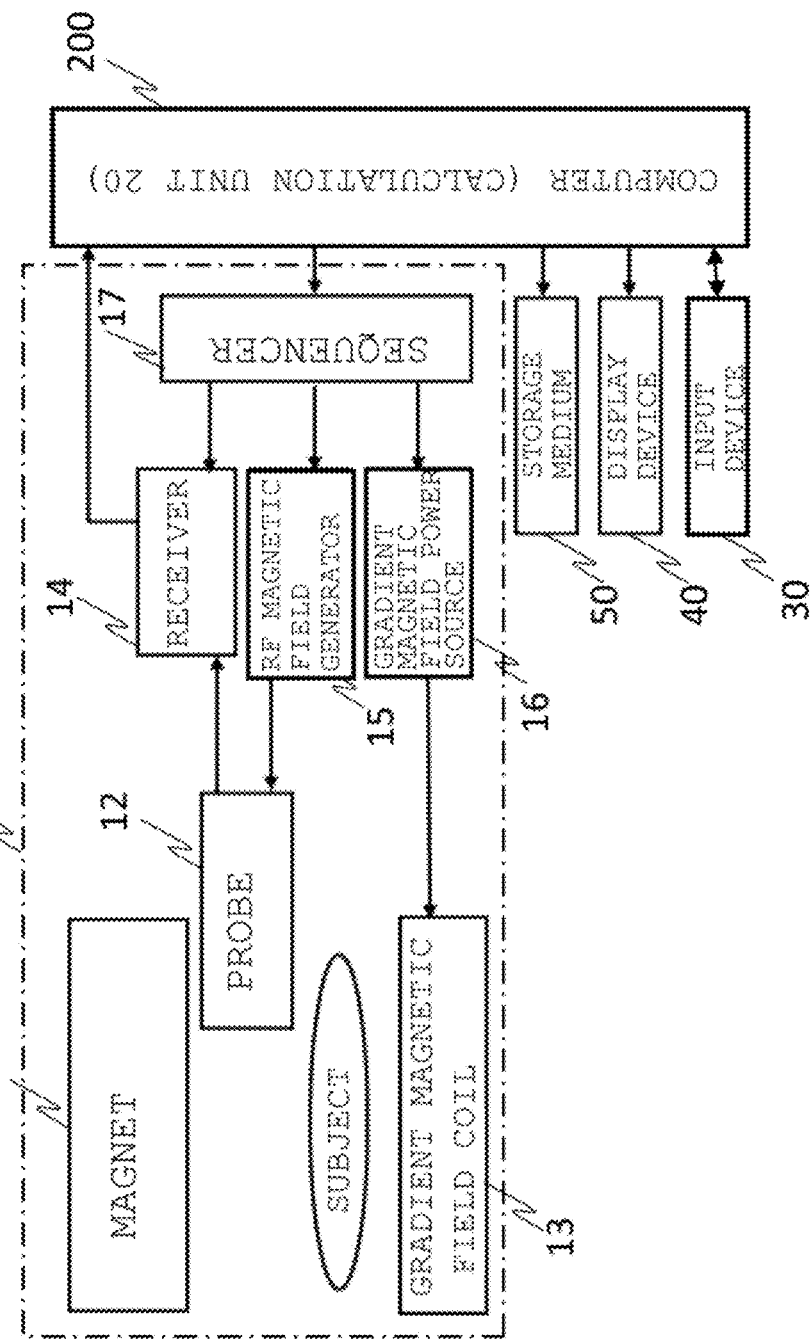
FIG. 1 illustrates an overview of an MRI apparatus.

First, a configuration of the MRI apparatus to which the present invention is applied will be described. As shown in FIG. 1, the configuration of the MRI apparatus 1 is similar to a configuration of general MRI apparatuses, including a magnet 11 configured to generate a uniform static magnetic field in examination space where a subject is placed, a gradient magnetic field coil 13 configured to provide a magnetic field gradient with respect to the static magnetic field generated by the magnet 11, a probe 12 having a transmission coil and a receiving coil, the transmission coil applying a pulse-like RF magnetic field to the subject and causing nuclear magnetic resonance to nucleus of atoms constituting tissue of the subject, and the receiving coil receiving a nuclear magnetic resonance signal generated from the subject, a receiver 14 connected to the receiving coil, an RF magnetic field generator 15 connected with the transmission coil, a gradient magnetic field power source 16 connected with the gradient magnetic field coil 13, a sequencer 17 configured to control the receiver 14, the RF magnetic field generator 15, and the gradient magnetic field power source 16 according to a predetermined pulse sequence, and a computer 200. The above-described elements excluding the computer 200 are collectively referred to as a measurement unit 10.

The nuclear magnetic resonance signals received by the receiver 14 of the measurement unit 10 are digitized and passed to the computer 200 as measurement data.

Structures, functions, and others of each part constituting the measurement unit 10 are similar to those in a publicly known MRI apparatus, and the present invention can be applied to various publicly known MRI apparatus types and elements. Thus, detailed descriptions of the measurement unit 10 will not be provided here.

The computer 200 functions as a calculation unit 20 for performing various operations including image generation on the measurement data of the measurement unit 10, and as a control system to control the entire MRI apparatus. The computer 200 can be configured by a general-purpose computer or a workstation provided with a CPU and a memory.

The computer 200 may be a computer or a workstation independent of the MRI apparatus, capable of exchanging data with the MRI apparatus. In this case, all or a part of the functions of the calculation unit 20 can be performed by an independent device (image analyzer). This type of image analyzer has a receiving unit for receiving data from the MRI apparatus, and implements an image analysis function similar to that of the computer 200, which will be described below.

It is also possible to employ hardware such as PLC (Programable logic controller), ASIC, and FPGA, to process the measurement data, and these are embraced in the calculation unit 20 in a broad sense.

The MRI apparatus according to the present embodiment features that the measurement unit 10 performs measurement using a pulse sequence of diffusion-weighted imaging (DWI), and the calculation unit 20 uses the measurement data obtained by the DWI to calculate a fluid parameter for detecting an abnormality in a flow of fluid such as blood or cerebrospinal fluid passing through the body of the subject. Therefore, the computer 200 sends a command to the sequencer 17 (measurement controller) and controls the measurement unit 10 to execute the DWI sequence under an imaging condition specified by a user via an input device (input unit) 30 or a similar unit. Then, using the measured data, the calculation unit 20 performs computations to calculate the fluid parameter as described above. If necessary, a parameter image having values of the calculated parameter as pixel values may be generated and displayed on a display device 40, and stored in a storage medium 50 or transferred to another storage device such as a medical information database.

Figure 2:
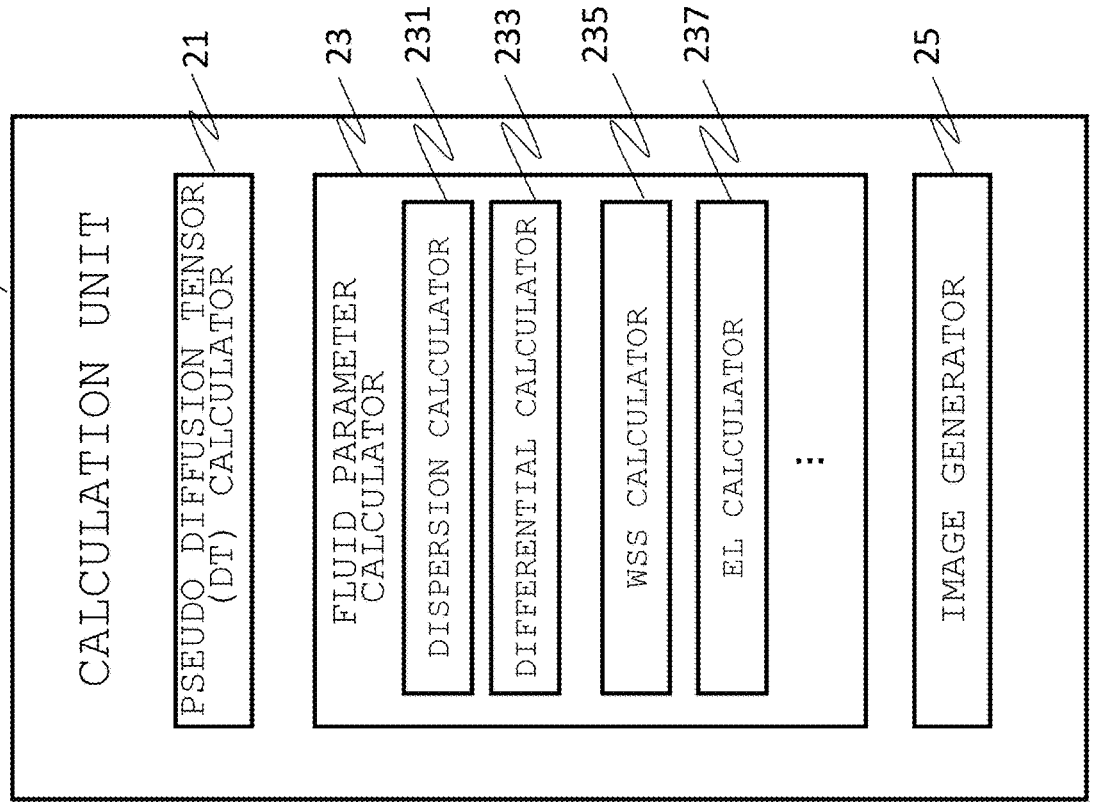
FIG. 2 is a functional block diagram of a calculation unit.

FIG. 2 is one example of a functional block diagram of the calculation unit 20 that implements the above functions. As illustrated, the calculation unit 20 comprises a DT calculator 21 configured to process the measurement data of DWI to calculate data including a pseudo diffusion tensor (tensor representing mixed information of a flow velocity and diffusion), a fluid parameter calculator 23 configured to calculate a fluid parameter using a fluid vector, and an image generator 25. The fluid parameter calculator 23 includes a dispersion calculator 231 configured to calculate dispersion of the flow velocity for each pixel (voxel of the DT image), a differential calculator 233 configured to calculate a differential vector of the flow velocity, using the dispersion calculated by the dispersion calculator 231 and an estimation model of the calculated dispersion and a distribution of the flow velocity (the shape of the distribution in the voxel), and various-parameter calculators configured to calculate individual fluid parameters using the differential vector. The fluid parameters include, in addition to WSS and EL, PG (pressure gradient) and OSI (oscillatory shear index), for instance. FIG. 2 illustrates only a WSS calculator 235 and an EL calculator 237 for calculating WSS and EL, respectively, as representative examples.

Figure 3:
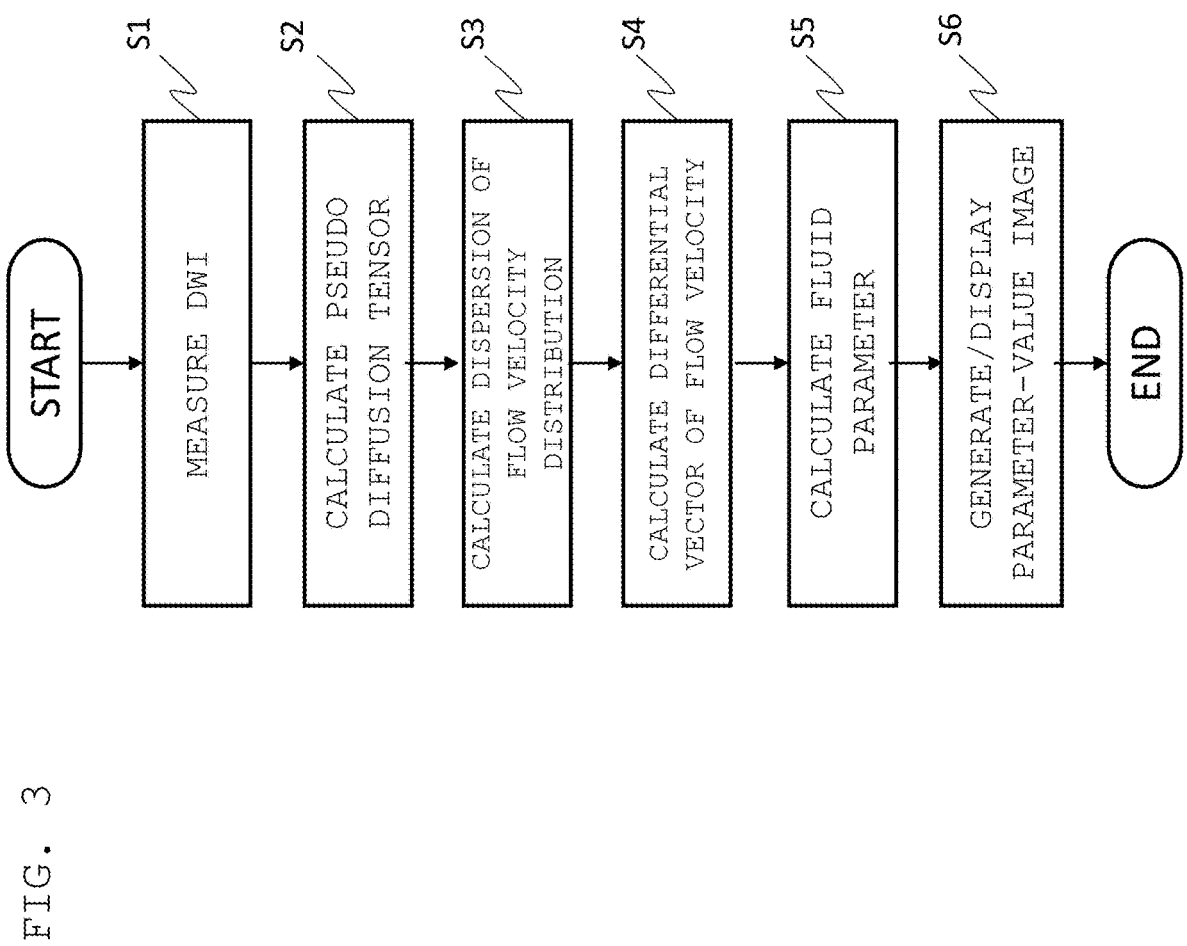
FIG. 3 is a flowchart illustrating a process of a fluid parameter calculator.

Functions of the DT calculator 21 for calculating a pseudo diffusion tensor from the measurement data of DWI are similar to those of conventional DTI, and these functions are well known. The MRI apparatus of the present embodiment, however, features that the fluid parameter calculator 23 utilizes the pseudo diffusion tensor obtained by DTI to calculate a highly accurate fluid parameter that cannot be obtained by the PC (phase contrast) method. The fluid parameter calculation will be described specifically in the embodiments described later. In the following, a process common to each embodiment will be described schematically with reference to FIG. 3.

Figure 4:
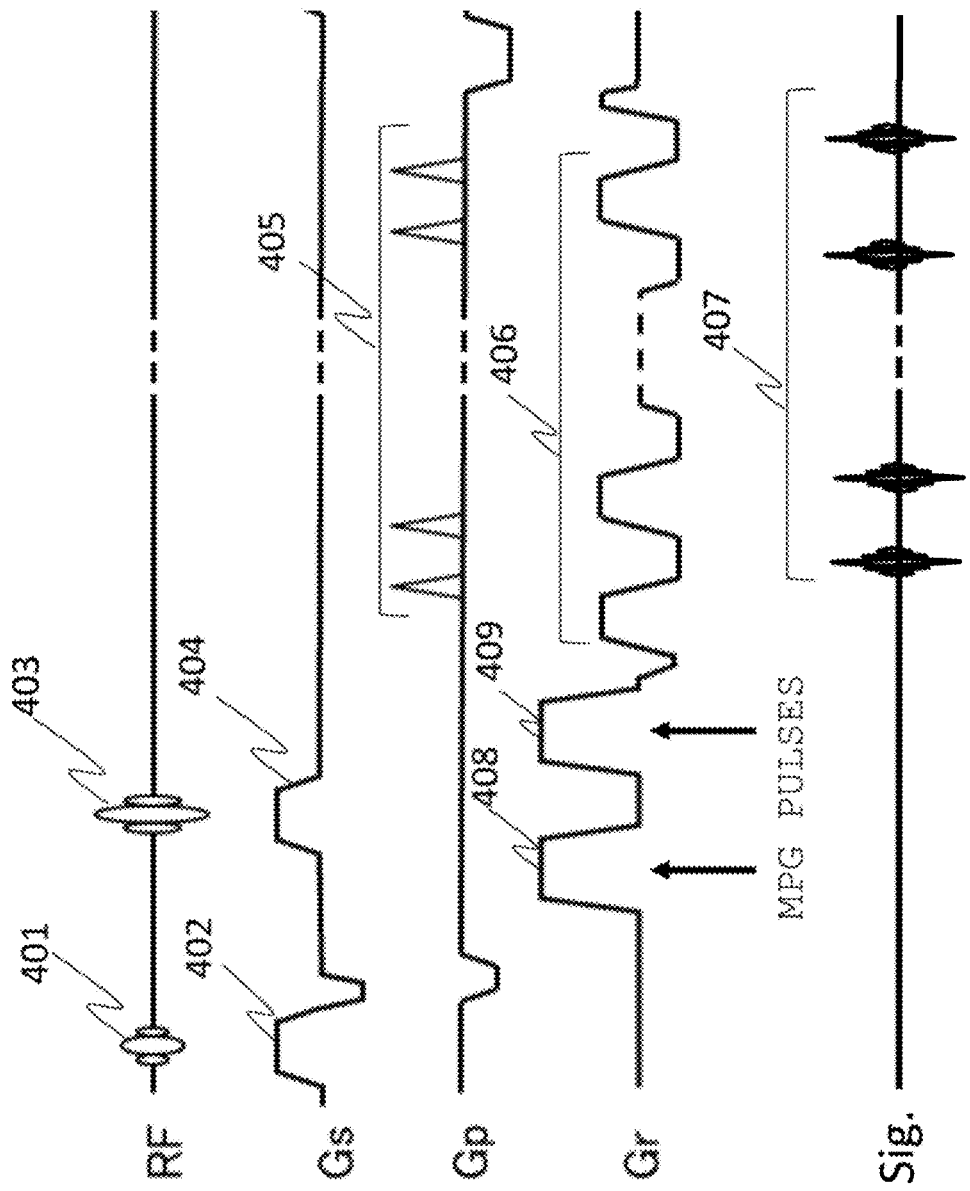
FIG. 4 illustrates an example of a pulse sequence used for diffusion tensor imaging.

Initially, under the control of the sequencer 17, the measurement unit 10 executes a pulse sequence of DWI (diffusion-weighted imaging) and collects measurement data (S1). An EPI (echo planar imaging) sequence is generally used as the pulse sequence of DWI, but other pulse sequences such as multi-shot EPI and SS (single shot) FSE may also be employed. FIG. 4 illustrates a typical pulse sequence of DWI. In the figure, the reference numerals 401 and 403 indicate RF pulses, 402 and 404 indicate slice gradient (Gs), the reference numeral 405 indicates phase-encoded gradient (Gp), 406 indicates readout gradient (Gr), and 407 indicates NMR signals.

As illustrated, the pulse sequence of DWI features that gradient magnetic field pulses (MPG pulses) 408 and 409 that promote phase diffusion of fluid, are applied before and after applying the 180-degree RF pulse 403 that reverses magnetization excited by the exciting RF pulse 401. Differentiating the intensity between the MPG pulses 408 and 409 causes phase dispersion corresponding to a difference in velocity of the fluid in the voxel (velocity dispersion), resulting in reduction of signal intensity of the voxel. In other words, this reduction in signal intensity can provide information on the velocity dispersion (pseudo diffusion) of the fluid in the voxel. That is, in the case where fluid is targeted, it is possible to obtain information of flow velocity dispersion by DWI. An indicator of the intensity of the MPG pulse is called b-value. When obtaining fluid parameters for the fluid at high velocity, a relatively low b-value is preferable. The b-value may be set in advance as multiple b-values within a predetermined range, or the user can set a specific b-value.

In addition, varying the axis along which the MPG pulse is applied enables obtainment of information regarding anisotropy of diffusion and pseudo diffusion. FIG. 4 illustrates an example where the MPG pulses are applied in the readout direction (Gr-axis). The diffusion tensor imaging (DTI) requires, however, application of MPG signals in six or more directions in order to calculate DT. Thus, the measurement is performed in the same manner as in FIG. 4 for a plurality of axes set in advance.

In the EPI sequence, phase-encoded gradient pulses 405 and reversed readout gradient pulses 406 are applied, after one excitation RF pulse, thereby obtaining a plurality of NMR signals 407 constituting one image. The NMR signals 407 are arranged at positions in the k-space determined by the applied phase encoding amount and the readout gradient magnetic field, passed to the computer 200 as digital data (measurement data), and in the computer 200, the calculation unit 20 performs various operations.

The calculation unit 20 calculates a diffusion tensor for each voxel (each pixel) first in the DT calculator 21 (S2).

Though a method for calculating the diffusion tensor DT is well known, it will be described briefly in the following. The diffusion tensor DT can be determined by obtaining the slope of the corresponding straight line expressed by the following Equation 1, from the signal intensity of multiple DWI taken by varying b-vector, and the diffusion tensor DT is expressed by a matrix of 3×3.

(Equation 1)

$$\ln(Si/S0) = -bGi^T \cdot DT \cdot Gi \quad (1)$$

$$DT = \begin{bmatrix} P_{xx} & P_{xy} & P_{xz} \\ P_{xy} & P_{yy} & P_{yz} \\ P_{xz} & P_{yz} & P_{zz} \end{bmatrix}$$

where $Si$ is the signal intensity obtained with a predetermined b-vector, b is the absolute value of the b-vector, $Gi$ is a unit vector representing an application direction of the gradient magnetic field of the b-vector. It is to be noted that there is also a method of expression where the b-value is a multi-dimensional numerical value, that is, synonymous with the b-vector.

Eigenvalues and eigenvectors can be obtained by diagonalizing this diffusion tensor DT. This conversion into the eigenvalues and eigenvectors allows obtainment of a principal axis of the diffusion tensor in the voxel, and the two axes perpendicular to the principal axis. It is also possible to obtain information such as an apparent diffusion coefficient ADC, using the eigenvector diagonal element.

Figure 5:
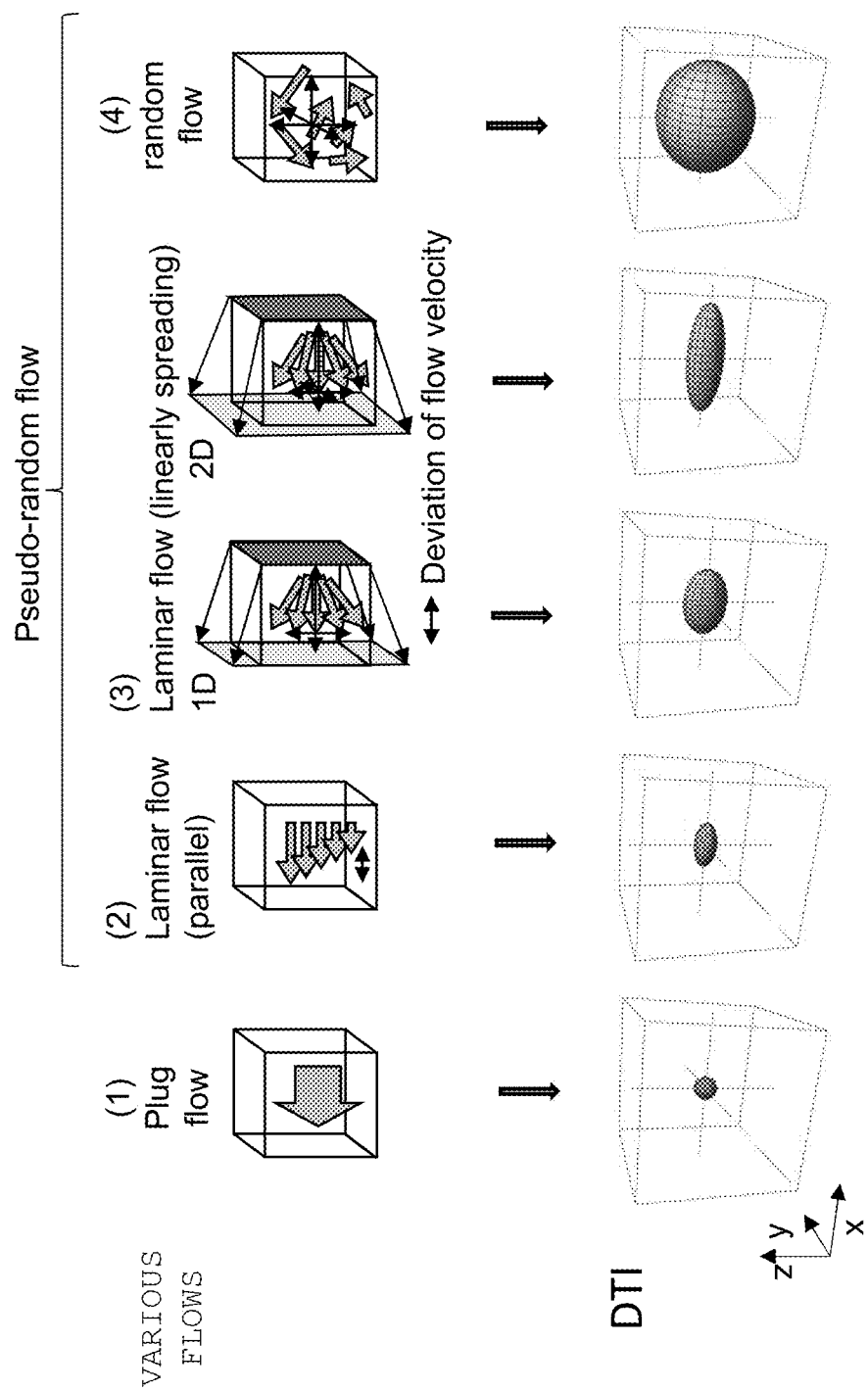
FIG. 5 illustrates relationships between various flows, and diffusion tensors (DT) respectively associated therewith.

The diffusion tensor is represented by an ellipsoidal model as shown in FIG. 5 (lower side), and the shape of the model varies depending on the type of the flow in the voxel as follows, for example; in the case the plug flow 1 that flows at the same velocity as shown in the left end of the upper side of the FIG. 5, the model becomes a small true spherical reflecting only molecular diffusion, in the cases of laminar flows 2 and 3 as in the three types of laminar flows in the center, the model becomes ellipsoidal with anisotropy, and in the case of isotopically random flow 4, the model becomes a large true spherical shape. DTI is provided to calculate diffusion tensors from signal values of the fluid as shown in the upper side of FIG. 5 and to obtain images as shown in the lower side of the figure. It is impossible, however, to calculate the fluid parameter as an indicator representing the state of the flow, directly from DTI.

The fluid parameter calculator 23 of the present embodiment assumes on a distribution of the flow velocity in the voxel, and calculates its dispersion and a flow velocity differential vector, thereby enabling calculation of the fluid parameters using the flow velocity differential vector.

Therefore, in the fluid parameter calculator 23, the dispersion calculator 231 first calculates dispersion of the flow velocity distribution p using the diffusion tensor DT of each voxel calculated by the DT calculator 21 (S3). Next, a differential value of the flow velocity is calculated using an assumed shape of the flow velocity distribution p and the calculated dispersion (S4). Next, the parameter calculators (235, 237, and so on) individually use the differential value of the flow velocity to calculate WSS, EL, and so on (S5).

Figure 6:
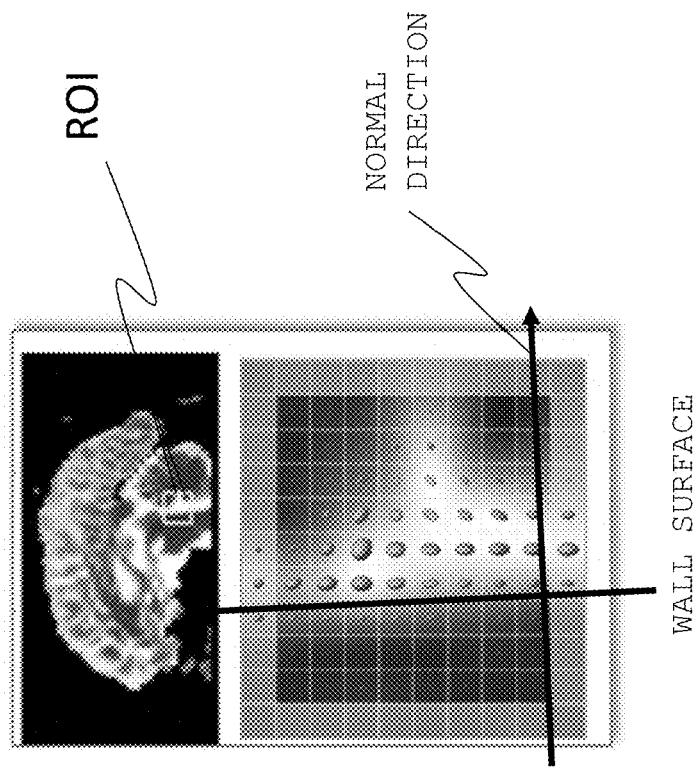
FIG. 6 illustrates an example of a brain image and its diffusion tensor image.

The image generator 25 generates a display image showing the values of the calculated parameters, together with a form image and DTI (diffusion tensor image) obtained by DWI (S6). FIG. 6 shows an example of the DTI being displayed. A sagittal cross section of a brain image is shown in the upper side of FIG. 6, and DTI of a portion surrounded by a square in the brain image is shown in the lower side of the figure. As illustrated, DTI is displayed in voxel units, and thus the wall surface through which the cerebrospinal fluid flows is delineated. It is also possible to present or identify the normal direction in which the wall shear stress should be calculated.

As described schematically so far, the MRI apparatus of the present embodiment can calculate a vector differential value from the diffusion vector obtained by the DWI measurement, using the estimated shape as the shape of the distribution of the fluid vector in the voxel, and the use of this differential value allows accurate calculation of the fluid parameter.

There will now be described specific embodiments of the processing according to the calculation unit 20.

First Embodiment

In the present embodiment, the flow of fluid is assumed as a linear flow, and a rectangular distribution is employed as a model of the distribution of the flow velocity.

Figure 7:
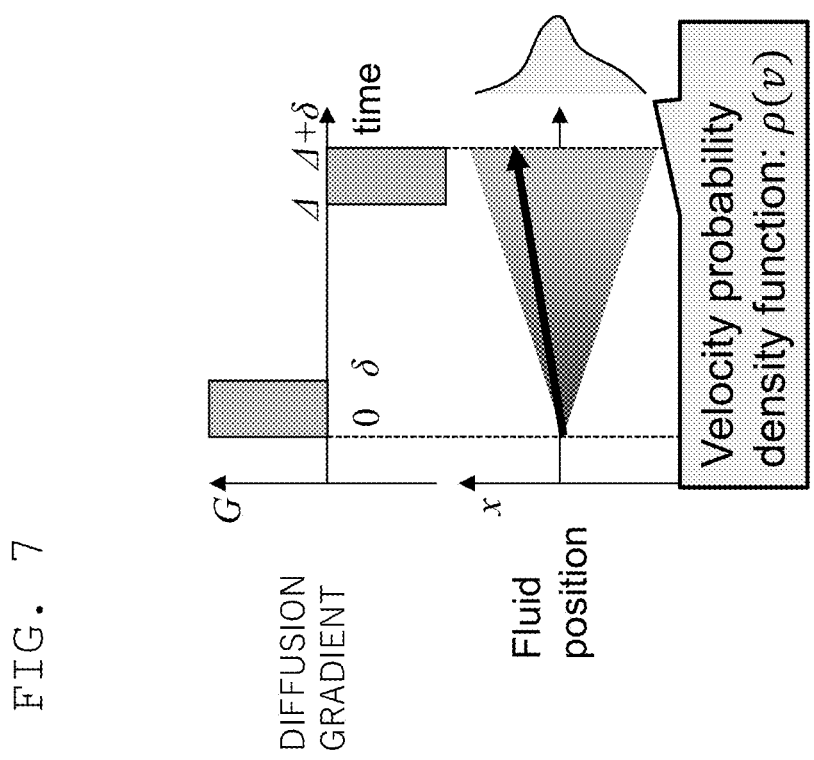
FIG. 7 schematically illustrates a relationship between a linear flow and a diffusion gradient.

The linear flow is a flow in which transport distance of the fluid is proportional to the elapse of time. When there is applied a pair of gradient magnetic fields (MPG pulses 408 and 409 in FIG. 4, being inverted positive and negative due to the 180° inverting pulse 403 therebetween) for diffusing the phase of the fluid, as shown in FIG. 7, the diffusion time τd is expressed by Equation 2 as follows:

$$\tau d = \Delta - \delta/3 \quad \text{(Equation 2)}$$

where δ is application time of the pulse, and Δ is the time from the first pulse to the second pulse.

The dispersion calculator 231 uses the diffusion time τd to calculate the dispersion Cov(ρ) of the flow velocity distribution ρ(v, xi) of each voxel. Given that the tensor is P when taking the limit as b decreases to zero, in the DT (3×3 matrix) calculated by the DT calculator 21 as shown in Equation 1, it has been found that P has the relationship with the dispersion Cov(ρ) of the flow velocity distribution ρ as the following equation (Non-Patent Document 1: Equation 3).

(Equation 3)

$$P = \frac{\tau_d}{2} \text{Cov}(\rho) + D \quad (3)$$

where τd is diffusion time, D is diffusion coefficient (the same shall apply hereinafter), and it is translated into a matrix form as follows:

$$\begin{bmatrix} P_{xx} & P_{xy} & P_{xz} \\ P_{xy} & P_{yy} & P_{yz} \\ P_{xz} & P_{yz} & P_{zz} \end{bmatrix} = $$

$$\frac{\tau_d}{2} \begin{bmatrix} \text{Cov}(\rho_x \rho_x) & \text{Cov}(\rho_x \rho_y) & \text{Cov}(\rho_x \rho_z) \\ \text{Cov}(\rho_x \rho_y) & \text{Cov}(\rho_y \rho_y) & \text{Cov}(\rho_y \rho_z) \\ \text{Cov}(\rho_x \rho_z) & \text{Cov}(\rho_y \rho_z) & \text{Cov}(\rho_z \rho_z) \end{bmatrix} + \begin{bmatrix} D_{xx} & D_{xy} & D_{xz} \\ D_{xy} & D_{yy} & D_{yz} \\ D_{xz} & D_{yz} & D_{zz} \end{bmatrix}$$

Depending on the conditions, this can be simplified as follows:

1) When Cov(ρ) is sufficiently larger than D, Equation 31 is established:

$$P = \frac{\tau_d}{2} \text{Cov}(\rho) \quad (31)$$

2) When Δ≫δ, approximation of τd=Δ is possible and thus Equation 32 is established:

$$P = \frac{\Delta}{2} \text{Cov}(\rho) \quad (32)$$

The dispersion calculator 231 uses Equation 3, or either of Equations 31 and 32, to calculate the dispersion Cov(ρ) of the flow velocity distribution ρ(v, xi) of each voxel. When Equation 3 is used, a process of subtracting the diffusion coefficient (tensor) D from the pseudo diffusion tensor P is performed, and for this process, there are two methods; a method of using prior information and a method of using additional measurement data. In the method using the prior information, the diffusion coefficient of free water, known in advance (e.g., diffusion coefficient of free water 3×10^(−9) m^2/s at a biological temperature of 37° C.), is subtracted from P. As for the method of using additional measurement data, it further includes two ways. One is a method of measuring a plurality of P while varying id, then fitting the measured data, thereby simultaneously obtaining Cov(ρ) and D. The other is a method of using MPG made up of a pair of bipolar pulses cancelling a velocity component, so as to measure only D, and then subtracting D from P. The specific process for calculating the dispersion Cov(ρ) is as follows. For the sake of simplicity, it will be described mainly in two dimensions.

In the case of laminar flow (being parallel) as shown in the upper side (2) of FIG. 5, when it is assumed as the laminar flow in the x-direction according to appropriate rotational coordinate transformation in order to provide generality, following equation is established:

$$\nabla V_{xx} = \nabla V_{yx} = \nabla V_{yy} = 0, \nabla V_{xy} = a$$

where a is a predetermined value, and $\nabla V_{ij}$ represents a value obtained by differentiating the flow velocity component in the i-direction with respect to the j-direction, and $$\text{Cov}(\rho_x \rho_x) = a^2, \text{Cov}(\rho_x \rho_y) = \text{Cov}(\rho_x \rho_y) = \text{Cov}(\rho_y \rho_y) = 0$$

is also established.

In the case of three dimensions, the y-direction and z-direction are indeterminate, and thus it is necessary to determine the ratio thereof. For example, the rate of change of Coy in the vicinity is calculated, and allocates values in the y-direction and in the z-direction according to its rate. When phase information has already been obtained by DTI, there may also be an approach that an average velocity of each voxel is calculated from the phase, and allocation is performed based on the square of the difference in velocity between neighboring voxels. The method of calculating the average velocity of each voxel from the phase is the same as the PC method. In addition, even when the PC method is used in combination as described later, it is also possible to take a method such as the aforementioned method where the average velocity of each voxel is calculated to perform allocation based on the square of the difference in velocity between neighboring voxels. Although it is not known whether the sign is positive or negative by the flow velocity differential vector calculated from the normal DTI, it becomes possible to give the positive sign or the negative sign, by applying the sign of the DTI or the sign of the PC used in combination.

In the case of laminar flow (linearly spreading) as shown in the center (3) of FIG. 5, the flow is regarded as a part of the fluid spring out from a certain point (radius r and angle θ), and the flow is transformed into a polar coordinate system. For incompressible liquids, the following equations are established from the relationship between the quantity of flow and cross-sectional area:

$$\nabla V_{rr} = (1/(2\pi r))' = -1/(2\pi r^2) \text{(in the case of 2}D\text{)}$$

$$\nabla V_{rr} = (1/(4\pi r^2))' = -1/(2\pi r^3) \text{(in the case of 3}D\text{)}$$

$$\nabla V_r \theta = \nabla V \theta r = \nabla V_v \theta \theta = 0$$

$$\text{Cov}(\rho_r \rho_r) = 1/(4\pi^2 r^4) \text{(in the case of 2}D\text{)}$$

$$\text{Cov}(\rho_r \rho_r) = 1/(4\pi^2 r^6) \text{(in the case of 3}D\text{)}$$

$$\text{Cov}(\rho_\theta \rho_\theta) = r^2 \theta^2, \text{Cov}(\rho_r \rho_\theta) = \text{Cov}(\rho_\theta \rho_r) = 0$$

In the case of three dimensions, similar to the case of laminar flow (being parallel), the y-direction and z-direction are indeterminate, and thus the ratio thereof is to be determined. For example, in the case where phase information is obtained by DTI for calculating the rate of change of Cov in the vicinity and performing allocation according to the rate, the average velocity in each voxel is calculated from the phase, and allocation is performed based on the square of the difference in velocity between neighboring voxels. In addition, even when the PC method is used in combination as described later, it is also possible to employ a method such as calculating the average velocity in each voxel and performing allocation based on the square of the difference in velocity between neighboring voxels.

Figure 8A:
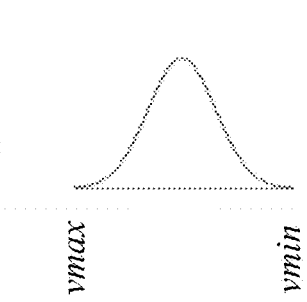
FIGS. 8A and 8B illustrate examples of an estimation model of a flow velocity distribution.

Next, the differential calculator 233 estimates a shape of the flow velocity distribution and calculates a flow velocity differential vector using the calculated dispersion Cov(ρ). Here, assuming that the shape of the flow velocity distribution ρ is a rectangular distribution, that is, as shown in FIG. 8A, the distribution is spatially linear in the voxel, the dispersion of the rectangular distribution and the flow velocity differential vector ∇V have the relationship of the following Equation 4, and the flow velocity differential vector ∇V is expressed by Equation 5.

$$\text{Cov}(\rho)=(v\ \text{max}-v\ \text{min})^2/12=(\nabla V \cdot \Delta x)^2 12 \quad \text{(Equation 4)}$$

$$\nabla V=\sqrt{(12\ \text{Cov}(\rho))}/\Delta x \quad \text{(Equation 5)}$$

In Equations 4 and 5, Δx is the voxel size.

The differential calculator 233 calculates the flow velocity differential vector according to Equation 5. Here, DT measured when b is sufficiently small can be regarded as P, so that when the DT obtained at a low b-value is substituted into Equation 5, as P in Equation 3, Equation 5 is expressed as follows:

$$\nabla V=\sqrt{(24(P-D)/\tau d)}/\Delta x \quad \text{(Equation 51)}$$

As shown in Equation 31, D can be ignored when P is sufficiently larger than D. Although the sign of the calculated ∇V is not known, it is possible to calculate the sign-independent fluid parameter by using ∇V.

The fluid parameter calculator 23 calculates various fluid parameters using thus calculated flow velocity differential vector.

For example, as shown in FIG. 6, the WSS calculator 235 first extracts the wall surface through which the fluid flows. For extracting the wall surface, there are considered a method of setting a threshold to MD (mean diffusivity) of DTI, and a method of setting a threshold to brightness, by separately measuring images emphasizing liquid, such as MRA (MR Angiography) and T2W imaging of intensity. Then, the normal vector n for the wall surface is calculated, and the flow velocity differential value in the normal direction is calculated. The WSS (wall shear stress) can be calculated by the following equation using the flow velocity differential value ∇V·n in the normal direction:

[Equation 6]

$$W = \mu w\left(\frac{|n|}{2}\right) \quad (6)$$

where W represents WSS, w represents the flow velocity differential value ∇V·n·μ is the viscosity (fixed value) of the fluid (for example, μ=0.004 Pa*s in the case of blood) (the same shall apply hereinafter).

The EL calculator 237 specifies a target area V and calculates an energy loss (EL) according to the following Equation 7:

[Equation 7]

$$EL = \int_V \mu \sum_{i,j=x,y,z} \frac{1}{2}(\nabla V_{i,j} + \nabla V_{j,i})^2 dV \quad (7)$$

The EL calculator 237 can also use another method mathematically equivalent to the above Equation 7. That is, each element of DTI or eigenvalues can be used directly, thereby allowing the flow velocity differential vector to be used implicitly. For example, Equation 7 is subjected to appropriate coordinate transformation to perform diagonalization, and then expanded to obtain one element $\nabla V_{i,j}^2$, and this element becomes equivalent to one element $P_{i,j}$ of DTI, except for its constant multiple. Here, the constant multiple is uniquely determined by assuming a rectangular distribution or a Gaussian distribution as the velocity distribution. Thus, EL may be calculated from the information obtained by DTI, without obtaining the flow velocity differential vector explicitly. FIG. 2 illustrates only the WSS calculator and the EL calculator, but as the fluid parameter, PG (pressure gradient) with respect to the direction n specified by the user may be calculated. A method of calculating the PG is expressed by ∇V·n.

The fluid parameters thus calculated are presented to the user such as displaying on the display device 40 together with the DTI shown in FIG. 6. This allows the user to see indicators regarding fluid abnormality along with DTI.

According to the present embodiment, the DTI data (pseudo diffusion tensor) and the estimation model for the flow velocity distribution of fluid are utilized, thereby obtaining the differential vector of the flow velocity, and it is possible to calculate the fluid parameters using the differential vector. Here, since the dispersion of the flow velocity distribution for calculating the differential vector can be directly measured by DTI, it is less susceptible to spatial resolution, unlike the PC method. Therefore, accuracy can be improved if the spatial resolution is the same as the other (e.g. PC method), and it is also possible to reduce the measurement time because the spatial resolution can be lowered.

First Modification of First Embodiment

In the first embodiment described above, there has been described the case where WSS and EL are used as the fluid parameters. In the case where motion gated imaging is performed at the time of DWI measurement and information regarding the motion has already been obtained, this information is added to enable calculation of another fluid parameter.

The motion gated imaging includes, as is well known, a (peripheral) cardiac gated imaging or ECG (electrocardiogram) gated imaging for performing measurement in accordance with heart beating or electrocardiogram, respiratory gated imaging in accordance with respiration, and further, there is a gated imaging that uses timing of both motions. The present embodiment is applicable to any of the gated imaging methods. As methods of the gated imaging, there are a measuring method using a gating signal (synchronizing signal) as a trigger, and a retrospective analysis method that uses gating signals to perform ex post analysis on the data continuously measured. As long as the gating signal information can be obtained, the method is not particularly limited.

The fluid parameters using the gating signal include, for example, TAWSS (time-averaged WSS) or OSI (oscillatory shear index). TAWSS can be calculated according to Equation 8 where W(t) is the WSS calculated at each time phase:

[Equation 8]

$$TAWSS = Ave(|W(t)|) = \int_0^T |W(t)| dt/T \qquad (8)$$

In addition, OSI can also be calculated from the following Equation 9:

[Equation 9]

$$OSI = (1 - Ave(W(t))/Ave(|W(t)|))/2 \qquad (9)$$
$$= \left(1 - \int_0^T W(t) dt/T \bigg/ \int_0^T |W(t)| dt/T\right)/2$$

Second Modification of First Embodiment

In the first embodiment, the estimation model of the distribution of the flow velocity is provided as a rectangular distribution, but the estimation model is not limited to the rectangular distribution. The distribution may be deformed in consideration of the shape and size of an organ through which the fluid flows. By changing the relational expression representing the distribution of the flow velocity, the fluid parameters can be calculated in the same manner as in the first embodiment.

Figure 8B:
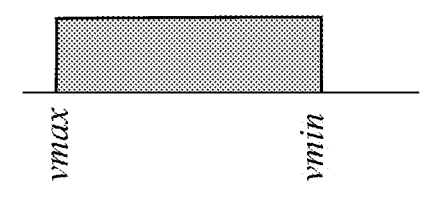

As an example, there will be described a case where a normal distribution as shown in FIG. 8B is used. When the flow velocity probability density function ρ(v) is approximated by the normal distribution (rounded down at ±3σ) and it is assumed to be spatially linearly distributed in the voxel, the dispersion and the flow velocity differential of this distribution have the following relation:

$$Cov(\rho) = \sigma^2 = (\nabla V \Delta x)^2/6 \qquad (10)$$

where Δx is the voxel size.

Thus, the above-described Equation 5 becomes the following Equation 52:

$$\nabla V = \sqrt{(6 \, Cov(\rho))}/\Delta x \qquad (52)$$

Equation 52 becomes the following Equation 53, using P measured by DTI (DT when b is sufficiently small) as in the case of the rectangular distribution:

$$\nabla V = \sqrt{(12(P-D)/\tau d)}/\Delta x \qquad (53)$$

Accordingly, a differential value ∇V can be calculated. Also in this modification, D may be ignored when P is sufficiently larger than D.

Thereafter, the fluid parameters such as WSS and EL are calculated using the obtained differential vector in the same manner as in the first embodiment.

Third Modification of First Embodiment

In this modification, the pulse sequence itself of the diffusion-weighted imaging is utilized to obtain phase contrast (velocity-dependent phase shift), and the flow velocity determined from the phase contrast is used in combination with or as an alternative to DTI of low b-value.

That is, the measurement unit 10 executes the pulse sequence of DWI in the same manner as in the first embodiment and acquires the measurement data of complex number values. The calculation unit 20 uses the phase information of the measurement data of the complex number values to calculate an average flow velocity of the fluid in each voxel within the examination target. The fluid parameter calculator 23 uses the pseudo diffusion tensor calculated by the DT calculator 21, the flow velocity calculated from the phase contrast, and the estimation model of the flow velocity distribution of the fluid, to calculate the flow velocity differential vector ∇V. Specifically, there are two methods for this calculation.

One of the two methods is to determine a direction ratio of the flow velocity differential vector, which becomes indeterminate when using only the pseudo diffusion tensor as described above, based on a difference relative to surrounding voxels, calculated from the flow velocity for each voxel obtained from the phase contrast. For example, the direction ratio is determined by the square of the difference in flow velocity. The other method uses the flow velocity obtained from the phase contrast, assuming that the difference from the surrounding voxels is ∇VP and the flow velocity differential vector obtained from the pseudo diffusion tensor by the above method is ∇VD, to obtain a mean or a weighted average of ∇VP and ∇VD, or select either of them according to a threshold of the flow velocity determined by the phase contrast. The latter method will be described in detail in the third embodiment where the measurement for the phase contrast is used in combination.

Similar to the first embodiment, the fluid parameters are calculated using the flow velocity differential vector in the subsequent steps.

Second Embodiment

Figure 9:
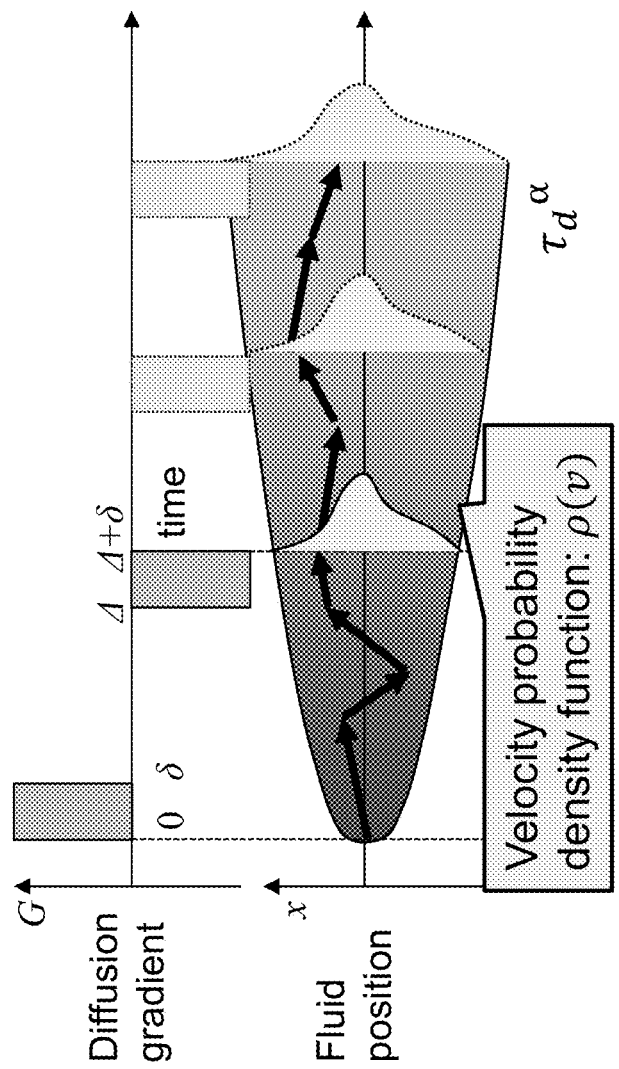
FIG. 9 schematically illustrates a flow, mixing the linear flow and the diffusion gradient.

In the first embodiment, a differential vector of the flow velocity is calculated, assuming that the flow is a linear flow. In the present embodiment, there are calculated fluid parameters of a complex flow that is intermediate between the linear flow and the diffusion. As shown in FIG. 9, a flow where the linear flow is mixed with the diffusion is generated, for example, when there is a vortex in the voxel, or when the flow is complicatedly bent. In this case, transport capacity is reduced, and the transport distance is not proportional to time.

In the present embodiment, as in the case of abnormal diffusion, an index α for modeling the time change is used to calculate the a power of the diffusion time (τd) "τd$^\alpha$" (0≤α≤1) and the dispersion Cov(ρ) according to the following Equation 33.

$$P = \tau d^\alpha/*(Cov(\rho)) + D \qquad (33)$$

Here, α=0 means diffusion, and α=1 means linear flow.

As in the case of the first embodiment or the modification thereof, the differential ∇V is calculated using the dispersion calculated on the basis of Equation 33, further the fluid parameters are calculated, and in the differential calculation, a rectangular shape or a Gaussian shape can be used as the estimated shape of the flow velocity distribution.

Figure 10:
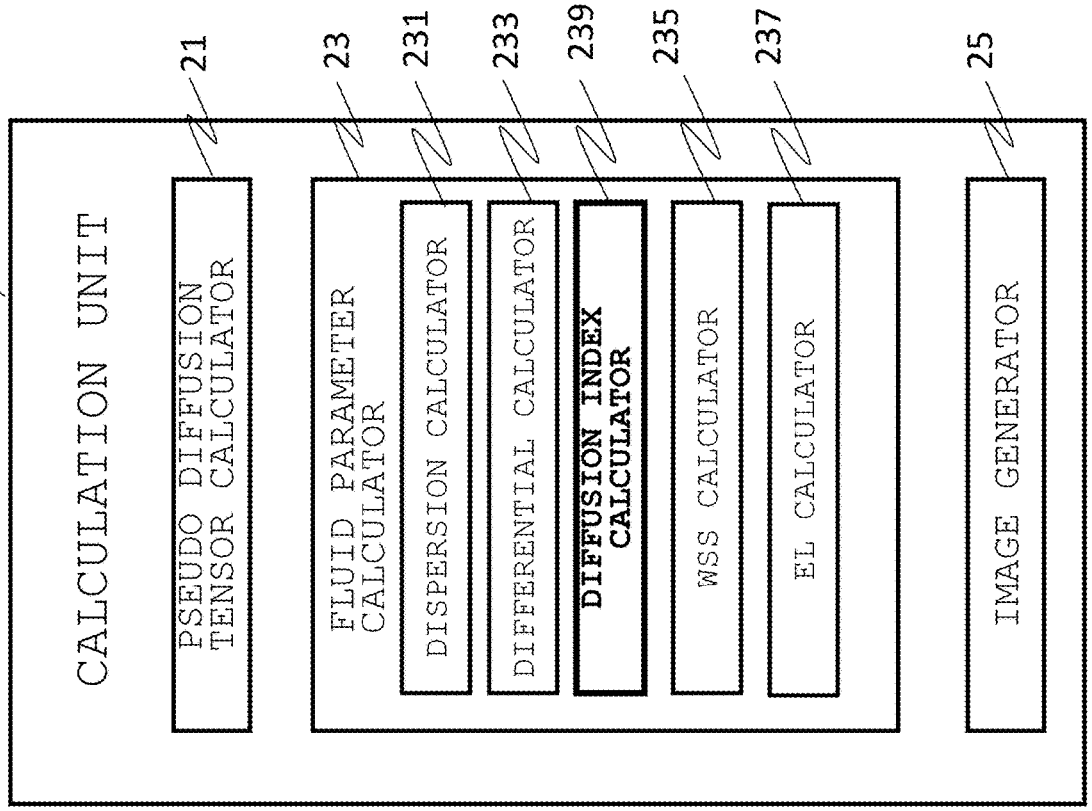
FIG. 10 is a functional block diagram showing an example of the calculation unit according to a second embodiment.

The measurement and calculation methods of the index α will be described. FIG. 10 is a functional block diagram of the fluid parameter calculator in this case. As illustrated, in the present embodiment, a diffusion index calculator 239 is added. Other elements are the same as those in FIG. 2 and these elements are denoted by the same reference numerals.

As one of the methods to estimate the diffusion element (index) α, the measurement is performed multiple times (e.g., three times) with different intervals of diffusion gradient (MPG: motion probing gradient). Assuming that the first interval is Δ1, the second interval is Δ2, and the third interval is Δ3 . . . , when the flow velocity of the fluid determined in each interval changes linearly with respect to the interval, the flow can be regarded as a linear flow, and α is calculated based on deviations from the linearity.

Subsequent processes are the same as in the first embodiment except that Equation 3 is replaced with Equation 33. In the present embodiment, there has been described the case where the index α is obtained by measurement. It is also possible to obtain the fluid parameters by fixing the index α as a biological model. Typically, fixing the index α as α=1 provides a model of the linear flow, and fixing the index α as α=0 provides a model of diffusion only.

Third Embodiment

Diffusion tensor imaging is generally known to be able to obtain a highly accurate DTI value (pseudo diffusion tensor) for a fluid at a low velocity. As for the fluid at a high flow velocity, the signal completely attenuates due to pseudo-diffusion, and thus the accuracy is reduced. On the other hand, in the PC method, when the flow velocity is low, the accuracy is reduced because the phase difference obtained by the measurement is small.

In the present embodiment, utilizing the characteristics of both, the two types of measurement are performed alternatively or combined, thereby improving the accuracy of the fluid parameter calculation in a wide range of velocity.

Figure 11:
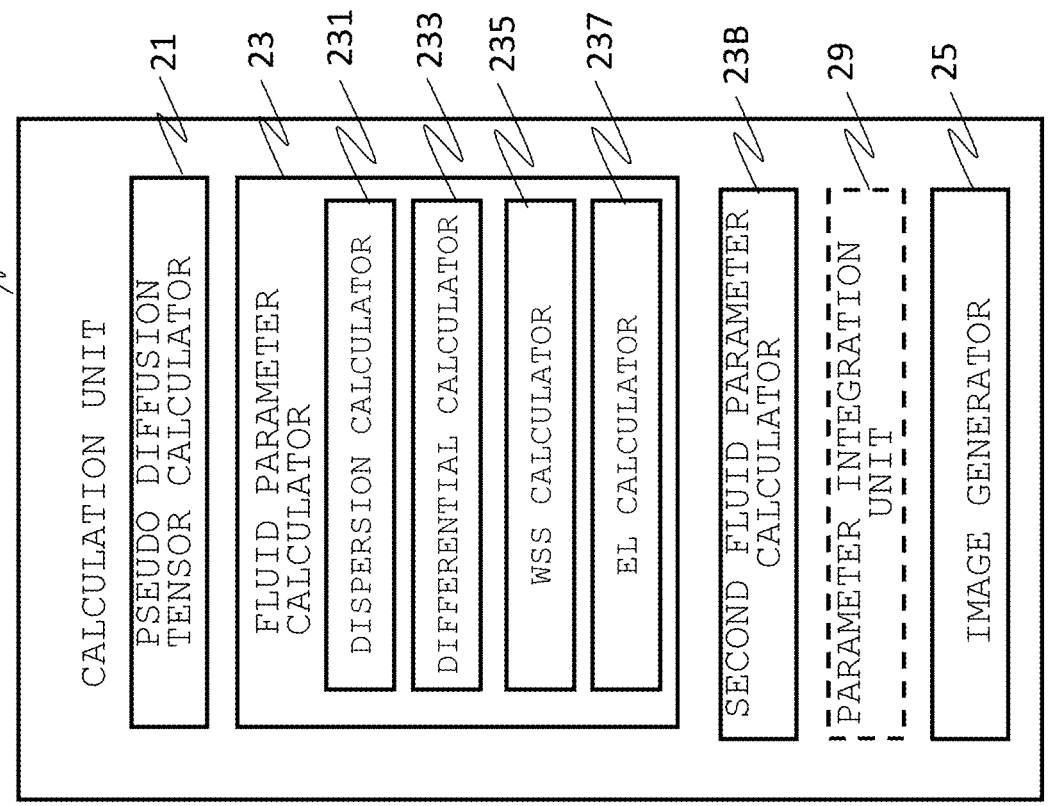
FIG. 11 is a functional block diagram of the calculation unit according to a third embodiment.

FIG. 11 is a functional block diagram showing the calculation unit of the present embodiment. In FIG. 11, elements having the same functions as those in FIG. 2 are denoted by the same reference numerals, and redundant description thereof will not be given.

As shown in FIG. 11, in addition to the fluid parameter calculator 23 using the DTI, the calculation unit 20 of the present embodiment is provided with a second fluid parameter calculator 23B for calculating the fluid parameters using the measurement data obtained by the PC method. It may also be configured to include a parameter integration unit 29 that integrates the results of the two fluid parameter calculators.

The second fluid parameter calculator 23B includes, although not illustrated, a flow velocity calculator 231B for calculating the flow velocity using the measurement data of the PC method, and a differential calculator 233B for calculating the differential vector of the flow velocity, and so on. The differential calculator 233B calculates the fluid parameters such as WSS and EL according to the above-described equations such as Equations 6 and 7, using the calculated differential vector of the flow velocity.

Which processing is performed, the processing by the fluid parameter calculator 23 or the processing of the second fluid parameter calculator 23B, may be selected by setting in advance a predetermined threshold value for the fluid velocity, or set in advance according to the type of the fluid of interest, such as blood or cerebrospinal fluid, arterial flow or vein flow, and so on. It is also possible that selection is made according to a user via an interface such as GUI, shown on the display device 40 and then, the selected result is set in the calculation unit 20.

FIGS. 12A and 12B illustrate examples of the GUI described above. In the example shown in FIGS. 12A and 12B, in the screen 1200 for setting the imaging conditions, calculation of the fluid parameters is already set as a default to be performed, or when accepting a user's instruction that the calculation of the fluid parameters is "required", there is displayed a GUI for selectively receiving information such as a site of the fluid, a type of the fluid, and the velocity of the fluid for calculating the fluid parameter according to the PC method.

When a predetermined flow velocity is set using this GUI, for example, the measurement unit 10 performs imaging of the PC method instead of the DWI imaging when the flow velocity is higher than the predetermined flow velocity, whereas the DWI imaging is performed when the provided flow velocity is lower than the predetermined flow velocity.

When the measurement unit 10 performs imaging by the PC method, the second fluid parameter calculator 23B calculates the fluid parameters by a conventional method (e.g., techniques described in Patent Document 1). On the other hand, when the measurement unit 10 performs the DWI imaging, in the same manner as the first and second embodiments, the DT calculator 21 creates DTI, and the fluid parameter calculator 23 calculates the fluid parameters using the information of DTI.

There has been described the example that the DWI imaging or the PC imaging is performed selectively. Both imaging methods may be used in combination, adding weight to the obtained result. In that case, the measurement unit 10 executes the DWI imaging and the PC imaging separately. The order of the imaging is not limited. The calculation unit 20 passes the data obtained by both imaging, respectively to the DT calculator 21 and to the second fluid parameter calculator 23B, and the processing by the fluid parameter calculator 23 and the processing by the second fluid parameter calculator 23B are performed in parallel.

In calculating the fluid parameter, the sign of positive or negative is not known by the flow velocity differential vector calculated from usual DTI, but the sign of PC is applied. Thus, it is also possible to obtain the fluid parameters requiring positive and negative signs for calculation.

Thereafter, the parameter integration unit 29 weights and adds the processed results of both the fluid parameter calculators 23 and 23B as shown in the following equation:

$$WSS = \omega 1 \cdot WSS_{DW} + \omega 2 WSS_{PC}$$

In the equation, $WSS_{DW}$ is the calculation result of the fluid parameter calculator 23, $WSS_{PC}$ is the calculation result of the fluid parameter calculator 23B. Here, WSS is shown as an example, and this calculation is applicable to other fluid parameters.

Weights ω1, ω2 may be constants, such as 0.5, 0.5, regardless of the type and velocity of the fluid. Alternatively, it is also possible to determine a predetermined weight in advance according to the type and velocity of the fluid, and to employ a weight in association with the type or the velocity of the fluid entered by a user through the GUI, or a weight in association with the fluid velocity calculated by the flow velocity calculator 231B.

According to the present embodiment, as a measurement method of basic data for calculating the fluid parameters, two imaging methods with different features are employed, and combining the calculation results of the two imaging methods enables calculation of fluid parameters with high accuracy, in response to a wide range of velocity and sites.

What is claimed is:
1. A magnetic resonance imaging apparatus comprising,
   a measurement unit configured to execute a pulse sequence of diffusion-weighted imaging including an MPG pulse to acquire measurement data, and a calculation unit configured to calculate a pseudo diffusion tensor of fluid within an examination target, using the measurement data acquired by the measurement unit, wherein the calculation unit includes a fluid parameter calculator configured to calculate a fluid parameter other than the pseudo diffusion tensor, using the pseudo diffusion tensor and an estimation model of an intra-voxel distribution of a flow velocity.

2. The magnetic resonance imaging apparatus according to claim 1, wherein the fluid parameter calculator calculates dispersion of a flow velocity distribution using the pseudo diffusion tensor, calculates a flow velocity differential vector using the dispersion of the flow velocity distribution thus calculated and the estimation model, and calculates the fluid parameter based on the flow velocity differential vector.

3. The magnetic resonance imaging apparatus according to claim 1, wherein the fluid parameter calculated by the fluid parameter calculator includes at least one of the followings; wall shear stress (WSS), kinetic energy (KE) or energy loss (EL), oscillatory shear index (OSI), and pressure gradient (PG).

4. The magnetic resonance imaging apparatus according to claim 1, wherein the calculation unit comprises an image generator configured to generate an image having values of the fluid parameter as pixel values, and to display the image on a display device.

5. The magnetic resonance imaging apparatus according to claim 1, wherein the estimation model used by the fluid parameter calculator has a flow velocity distribution being a rectangular distribution.

6. The magnetic resonance imaging apparatus according to claim 1, wherein the estimation model used by the fluid parameter calculator has a flow velocity distribution being a Gaussian distribution.

7. The magnetic resonance imaging apparatus according to claim 1, wherein the estimation model includes an index indicating deviations from linearity in fluid, and the calculation unit calculates the index from the pseudo diffusion tensor.

8. The magnetic resonance imaging apparatus according to claim 7, wherein the calculation unit calculates the index from the pseudo diffusion tensors calculated at multiple diffusion times.

9. The magnetic resonance imaging apparatus according to claim 1, wherein the measurement unit collects the measurement data by performing the diffusion-weighted imaging in sync with a periodic motion of the examination target, and the fluid parameter calculator calculates the fluid parameter with information of the periodic motion.

10. The magnetic resonance imaging apparatus according to claim 1, wherein the measurement unit configured to execute the pulse sequence of the diffusion-weighted imaging to acquire measurement data of complex number values, the calculation unit calculates the flow velocity of fluid within the examination target, using phase information of the measurement data of the complex number values, and the fluid parameter calculator calculates the fluid parameter, using the pseudo diffusion tensor, the flow velocity, and the estimation model.

11. The magnetic resonance imaging apparatus according to claim 1, wherein the measurement unit performs a first measurement using the pulse sequence of the diffusion-weighted imaging and a second measurement using the pulse sequence of a phase contrast method, and the calculation unit further comprises a second fluid parameter calculator configured to calculate the fluid parameter, using the measurement data obtained by the second measurement.

12. The magnetic resonance imaging apparatus according to claim 11, wherein the calculation unit further comprises a parameter integration unit configured to integrate the fluid parameter calculated by the fluid parameter calculator, with the fluid parameter calculated by the second fluid parameter calculator.

13. The magnetic resonance imaging apparatus according to claim 11, further comprising, an input unit configured to receive a condition regarding the fluid as a measurement target, wherein the measurement unit selectively performs the pulse sequence of the diffusion-weighted imaging and the pulse sequence of the phase contrast method, according to the condition received by the input unit.

14. An image analyzer comprising, a receiving unit configured to receive measurement data measured in a magnetic resonance imaging apparatus or a value of a pseudo diffusion tensor calculated from the measurement data, and a calculation unit configured to calculate a fluid parameter, using the measurement data or the value of the pseudo diffusion tensor received by the receiving unit, wherein the calculation unit includes a fluid parameter calculator configured to calculate the fluid parameter as an indicator representing a flow characteristic of fluid, using the pseudo diffusion tensor and an estimation model of a flow velocity distribution.

15. The image analyzer according to claim 14, wherein the fluid parameter calculator further comprises, a dispersion calculator configured to calculate dispersion of the flow velocity distribution from the pseudo diffusion tensor, and a differential calculator configured to calculate a flow velocity differential vector, using the dispersion of the flow velocity distribution thus calculated and the estimation model.

16. A fluid analysis method using a diffusion tensor image of an examination target containing fluid, the diffusion tensor image being acquired by a magnetic resonance imaging apparatus, comprising, calculating dispersion of a flow velocity distribution of the fluid, using the diffusion tensor image, calculating a differential value of a flow velocity, using the dispersion and a distribution shape of intra-voxel flow velocity, and calculating a fluid parameter indicating a flow characteristic of the fluid, using the differential value.

* * * * *